(12) United States Patent
Kohl et al.

(10) Patent No.: US 8,679,795 B2
(45) Date of Patent: Mar. 25, 2014

(54) THERMOSTABLE XYLANASE FOR THE SELECTIVE HYDROLYSIS OF PENTOSE-CONTAINING POLYSACCHARIDES

(75) Inventors: Andreas Kohl, München (DE); Isabel Unterstrasser, Rimsting (DE); Markus Rarbach, München (DE); Andre Koltermann, Icking (DE); Christoph Reisinger, München (DE); Thomas Brück, Ebenhausen (DE); Ulrich Kettling, München (DE); Gudmundur O. Hreggvidsson, Reykjavik (IS); Olafur H. Fridjonsson, Reykjavik (IS)

(73) Assignee: Sud-Chemie IP GmbH & Co. KG, Munich (DE)

( * ) Notice: Subject to any disclaimer, the term of this patent is extended or adjusted under 35 U.S.C. 154(b) by 0 days.

(21) Appl. No.: 13/517,344

(22) PCT Filed: Dec. 15, 2010

(86) PCT No.: PCT/EP2010/069736
§ 371 (c)(1),
(2), (4) Date: Jan. 15, 2013

(87) PCT Pub. No.: WO2011/080078
PCT Pub. Date: Jul. 7, 2011

(65) Prior Publication Data
US 2013/0109062 A1    May 2, 2013

(30) Foreign Application Priority Data

Dec. 21, 2009 (EP) .................. 09180210

(51) Int. Cl.
*C12N 9/24* (2006.01)

(52) U.S. Cl.
USPC ................ 435/99; 435/208; 435/254.2

(58) Field of Classification Search
USPC .................................. 435/99, 254.2
See application file for complete search history.

(56) References Cited

PUBLICATIONS

Subramaniyan and Prema. Biotechnology of Microbial Xylanases: Enzymology, Molecular Biology, and Application. Critical Reviews in Biotechnology, 22(1):33-64, 2002.*
NCBI GenBank Accession: ACZ42385 Lucas et al. Nov. 12, 2009.

* cited by examiner

*Primary Examiner* — Tekchand Saidha
*Assistant Examiner* — Rama P Ramanujam
(74) *Attorney, Agent, or Firm* — McCarter & English, LLP

(57) ABSTRACT

The present invention relates to polypeptides having xylanase activity and nucleic acid sequences encoding such polypeptides. The invention also relates to nucleic acid constructs, vectors, and host cells comprising the nucleic acid constructs as well as methods for producing and using the polypeptides. One specific application of the xylanase is the selective hydrolysis of pentose sugar components of hemicellulose-containing plant biomass. The nucleotide sequence may be used for the production of the xylanase or optimized mutants thereof.

12 Claims, 7 Drawing Sheets

SEQUENCE LISTING

<160> NUMBER OF SEQ ID NOS: 8

<210> SEQ ID NO 1
<211> LENGTH: 307
<212> TYPE: PRT
<213> ORGANISM: Unknown
<220> FEATURE:
<223> OTHER INFORMATION: Originating from a metagenomic clone library
      without identification of the source organism.

<400> SEQUENCE: 1

```
Leu Ser Asn Glu Glu Gln Tyr Gln Leu Val Val Arg Glu Phe Asn
1               5                   10                  15

Ser Val Thr Pro Glu Asn Val Met Lys Trp Asp Thr Ile Glu Pro Ile
            20                  25                  30

Arg Gly Gln Leu Asn Phe Glu Pro Ala Asp Gln Leu Val Asp Phe Ala
        35                  40                  45

Arg Arg His Gly Gln Ile Val Arg Glu His Thr Leu Val Trp His Asn
    50                  55                  60

Gln Leu Pro Ser Trp Leu Thr Asn Gly Asn Phe Thr Asn Gln Glu Leu
```

```
                65                  70                  75                  80
Glu Glu Ile Leu Arg Gln His Ile Tyr Asp Val Val Arg His Phe Lys
                    85                  90                  95
Gly Lys Val Tyr Ser Trp Asp Val Val Asn Glu Pro Leu Asn Glu Asp
                100                 105                 110
Gly Thr Leu Arg Asp Ser Ile Trp Leu Arg Ala Ile Gly Pro Asp Tyr
                115                 120                 125
Ile Ala Lys Ala Phe Gln Trp Ala His Glu Ala Asp Pro His Ala Lys
            130                 135                 140
Leu Tyr Ile Asn Asp Tyr Asn Ile Glu Trp Ile Gly Pro Lys Ser Asn
145                 150                 155                 160
Gly Met Tyr Glu Leu Val Lys Ser Leu Lys Glu Ala Gly Val Pro Ile
                165                 170                 175
Asp Gly Val Gly Phe Gln Gly His Leu Gly Ile Gln Tyr Gly Phe Pro
                180                 185                 190
Gly Asp Ile Gln Gln Asn Ile Gln Arg Phe Ala Asp Leu Gly Leu Asp
                195                 200                 205
Val Ala Leu Ser Glu Val Asp Val Arg Met Ile Leu Pro Val Thr Gln
            210                 215                 220
Glu Lys Leu Ala Thr Gln Ala Glu Tyr Tyr Arg Arg Leu Met Asp Ala
225                 230                 235                 240
Cys Leu Asn Val Arg Arg Cys Val Ser Phe Thr Val Trp Gly Phe Thr
                245                 250                 255
Asp Ala His Ser Trp Val Pro Gly Phe Phe Gln Gly Gln Gly Ala Ala
                260                 265                 270
Thr Ile Phe Asp Glu Asn Tyr Gln Pro Lys Pro Ala Tyr Phe Ala Leu
                275                 280                 285
Lys Asp Glu Leu Thr Glu Arg Ser Gly Arg Pro Gln Gly Lys His Tyr
            290                 295                 300
Arg Asn Glu
305

<210> SEQ ID NO 2
<211> LENGTH: 330
<212> TYPE: PRT
<213> ORGANISM: Unknown
<220> FEATURE:
<223> OTHER INFORMATION: Originating from a metagenomic clone library
      without identification of the source organism.

<400> SEQUENCE: 2

Leu Leu Gly Leu Arg Asp Tyr Ala Ala Arg Thr His Leu Ser Ile Gly
1               5                   10                  15
Thr Ala Val Asp Val Asn Ala Leu Ser Asn Glu Gln Tyr Gln Leu
                20                  25                  30
Val Val Val Arg Glu Phe Asn Ser Val Thr Pro Glu Asn Val Met Lys
                35                  40                  45
Trp Asp Thr Ile Glu Pro Ile Arg Gly Gln Leu Asn Phe Glu Pro Ala
            50                  55                  60
Asp Gln Leu Val Asp Phe Ala Arg Arg His Gly Gln Ile Val Arg Glu
65                  70                  75                  80
His Thr Leu Val Trp His Asn Gln Leu Pro Ser Trp Leu Thr Asn Gly
                85                  90                  95
Asn Phe Thr Asn Gln Glu Leu Glu Glu Ile Leu Arg Gln His Ile Tyr
                100                 105                 110
Asp Val Val Arg His Phe Lys Gly Lys Val Tyr Ser Trp Asp Val Val
```

```
                115                 120                 125
Asn Glu Pro Leu Asn Glu Asp Gly Thr Leu Arg Asp Ser Ile Trp Leu
130                 135                 140

Arg Ala Ile Gly Pro Asp Tyr Ile Ala Lys Ala Phe Gln Trp Ala His
145                 150                 155                 160

Glu Ala Asp Pro His Ala Lys Leu Tyr Ile Asn Asp Tyr Asn Ile Glu
                165                 170                 175

Trp Ile Gly Pro Lys Ser Asn Gly Met Tyr Glu Leu Val Lys Ser Leu
            180                 185                 190

Lys Glu Ala Gly Val Pro Ile Asp Gly Val Gly Phe Gln Gly His Leu
        195                 200                 205

Gly Ile Gln Tyr Gly Phe Pro Gly Asp Ile Gln Gln Asn Ile Gln Arg
    210                 215                 220

Phe Ala Asp Leu Gly Leu Asp Val Ala Leu Ser Glu Val Asp Val Arg
225                 230                 235                 240

Met Ile Leu Pro Val Thr Gln Glu Lys Leu Ala Thr Gln Ala Glu Tyr
                245                 250                 255

Tyr Arg Arg Leu Met Asp Ala Cys Leu Asn Val Arg Arg Cys Val Ser
            260                 265                 270

Phe Thr Val Trp Gly Phe Thr Asp Ala His Ser Trp Val Pro Gly Phe
        275                 280                 285

Phe Gln Gly Gln Gly Ala Ala Thr Ile Phe Asp Glu Asn Tyr Gln Pro
    290                 295                 300

Lys Pro Ala Tyr Phe Ala Leu Lys Asp Glu Leu Thr Glu Arg Ser Gly
305                 310                 315                 320

Arg Pro Gln Gly Lys His Tyr Arg Asn Glu
                325                 330

<210> SEQ ID NO 3
<211> LENGTH: 331
<212> TYPE: PRT
<213> ORGANISM: Unknown
<220> FEATURE:
<223> OTHER INFORMATION: Originating from a metagenomic clone library
      without identification of the source organism.

<400> SEQUENCE: 3

Lys Arg Leu Gly Leu Arg Asp Tyr Ala Ala Arg Thr His Leu Ser Ile
1               5                   10                  15

Gly Thr Ala Val Asp Val Asn Ala Leu Ser Asn Glu Glu Gln Tyr Gln
            20                  25                  30

Leu Val Val Arg Glu Phe Asn Ser Val Thr Pro Glu Asn Val Met
        35                  40                  45

Lys Trp Asp Thr Ile Glu Pro Ile Arg Gly Gln Leu Asn Phe Glu Pro
    50                  55                  60

Ala Asp Gln Leu Val Asp Phe Ala Arg Arg His Gly Gln Ile Val Arg
65                  70                  75                  80

Glu His Thr Leu Val Trp His Asn Gln Leu Pro Ser Trp Leu Thr Asn
                85                  90                  95

Gly Asn Phe Thr Asn Gln Glu Leu Glu Glu Ile Leu Arg Gln His Ile
            100                 105                 110

Tyr Asp Val Val Arg His Phe Lys Gly Lys Val Tyr Ser Trp Asp Val
        115                 120                 125

Val Asn Glu Pro Leu Asn Glu Asp Gly Thr Leu Arg Asp Ser Ile Trp
    130                 135                 140

Leu Arg Ala Ile Gly Pro Asp Tyr Ile Ala Lys Ala Phe Gln Trp Ala
```

```
145                 150                 155                 160
His Glu Ala Asp Pro His Ala Lys Leu Tyr Ile Asn Asp Tyr Asn Ile
                165                 170                 175

Glu Trp Ile Gly Pro Lys Ser Asn Gly Met Tyr Glu Leu Val Lys Ser
            180                 185                 190

Leu Lys Glu Ala Gly Val Pro Ile Asp Gly Val Gly Phe Gln Gly His
        195                 200                 205

Leu Gly Ile Gln Tyr Gly Phe Pro Gly Asp Ile Gln Gln Asn Ile Gln
    210                 215                 220

Arg Phe Ala Asp Leu Gly Leu Asp Val Ala Leu Ser Glu Val Asp Val
225                 230                 235                 240

Arg Met Ile Leu Pro Val Thr Gln Glu Lys Leu Ala Thr Gln Ala Glu
                245                 250                 255

Tyr Tyr Arg Arg Leu Met Asp Ala Cys Leu Asn Val Arg Arg Cys Val
            260                 265                 270

Ser Phe Thr Val Trp Gly Phe Thr Asp Ala His Ser Trp Val Pro Gly
        275                 280                 285

Phe Phe Gln Gly Gln Gly Ala Ala Thr Ile Phe Asp Glu Asn Tyr Gln
    290                 295                 300

Pro Lys Pro Ala Tyr Phe Ala Leu Lys Asp Glu Leu Thr Glu Arg Ser
305                 310                 315                 320

Gly Arg Pro Gln Gly Lys His Tyr Arg Asn Glu
                325                 330

<210> SEQ ID NO 4
<211> LENGTH: 414
<212> TYPE: PRT
<213> ORGANISM: Unknown
<220> FEATURE:
<223> OTHER INFORMATION: Originating from a metagenomic clone library
      without identification of the source organism.

<400> SEQUENCE: 4

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Leu Gly Leu Arg Asp Tyr Ala Ala Arg Thr His
                85                  90                  95

Leu Ser Ile Gly Thr Ala Val Asp Val Asn Ala Leu Ser Asn Glu Glu
            100                 105                 110

Gln Tyr Gln Leu Val Val Arg Glu Phe Asn Ser Val Thr Pro Glu
        115                 120                 125

Asn Val Met Lys Trp Asp Thr Ile Glu Pro Ile Arg Gly Gln Leu Asn
    130                 135                 140

Phe Glu Pro Ala Asp Gln Leu Val Asp Phe Ala Arg Arg His Gly Gln
145                 150                 155                 160

Ile Val Arg Glu His Thr Leu Val Trp His Asn Gln Leu Pro Ser Trp
                165                 170                 175

Leu Thr Asn Gly Asn Phe Thr Asn Gln Glu Leu Glu Glu Ile Leu Arg
```

```
                    180             185             190
Gln His Ile Tyr Asp Val Val Arg His Phe Lys Gly Lys Val Tyr Ser
            195             200             205
Trp Asp Val Val Asn Glu Pro Leu Asn Glu Asp Gly Thr Leu Arg Asp
        210             215             220
Ser Ile Trp Leu Arg Ala Ile Gly Pro Asp Tyr Ile Ala Lys Ala Phe
225             230             235             240
Gln Trp Ala His Glu Ala Asp Pro His Ala Lys Leu Tyr Ile Asn Asp
            245             250             255
Tyr Asn Ile Glu Trp Ile Gly Pro Lys Ser Asn Gly Met Tyr Glu Leu
        260             265             270
Val Lys Ser Leu Lys Glu Ala Gly Val Pro Ile Asp Gly Val Gly Phe
            275             280             285
Gln Gly His Leu Gly Ile Gln Tyr Gly Phe Pro Gly Asp Ile Gln Gln
        290             295             300
Asn Ile Gln Arg Phe Ala Asp Leu Gly Leu Asp Val Ala Leu Ser Glu
305             310             315             320
Val Asp Val Arg Met Ile Leu Pro Val Thr Gln Glu Lys Leu Ala Thr
                325             330             335
Gln Ala Glu Tyr Tyr Arg Arg Leu Met Asp Ala Cys Leu Asn Val Arg
            340             345             350
Arg Cys Val Ser Phe Thr Val Trp Gly Phe Thr Asp Ala His Ser Trp
        355             360             365
Val Pro Gly Phe Phe Gln Gly Gln Gly Ala Ala Thr Ile Phe Asp Glu
    370             375             380
Asn Tyr Gln Pro Lys Pro Ala Tyr Phe Ala Leu Lys Asp Glu Leu Thr
385             390             395             400
Glu Arg Ser Gly Arg Pro Gln Gly Lys His Tyr Arg Asn Glu
                405             410

<210> SEQ ID NO 5
<211> LENGTH: 924
<212> TYPE: DNA
<213> ORGANISM: Unknown
<220> FEATURE:
<223> OTHER INFORMATION: Originating from a metagenomic clone library
      without identification of the source organism.

<400> SEQUENCE: 5
ctttctaatg aagaacaata tcagctggtg gtggtcagag aattcaatag tgttacccca     60
gaaaatgtca tgaatgggga tactattgag cccatacgtg gtcagctaaa ttttgagcca    120
gcagatcagc tcgtagattt tgcacggcgg catggtcaga tagtgagaga gcacacactc    180
gtctggcata accaactgcc cagctggttg acaaatggta actttaccaa ccaggagctg    240
gaggaaatac tgcgacagca catctatgat gttgtaaggc atttcaaggg caaggtgtat    300
tcttgggacg tagtgaacga gcccctgaat gaagatggta ccctaaggga tagcatatgg    360
cttagggcta ttggtccgga ttacatagcc aaagctttcc aatgggcgca cgaggctgat    420
ccacatgcca aactctacat caatgactac aacattgagt ggatcgggcc taagagcaat    480
ggaatgtacg agctggtgaa gagtctcaag gaagcaggtg tgcctatcga tggcgtggga    540
tttcaaggac atctcggcat acagtatgga tttcctgggg atattcaaca gaatattcag    600
agatttgctg atctgggatt ggatgtggct ctgtctgagg tggatgtgcg catgattcta    660
cctgttaccc aagagaaact tgctacacag gctgagtatt accgtcgact tatggatgct    720
tgtctgaatg tacgacgatg cgtatctttc acagtgtggg gattcaccga tgctcactca    780
```

```
tgggtacccg gattcttcca aggacaaggt gcggccacta tatttgatga gaattatcag      840
ccgaaaccag cgtattttgc tttgaaggat gaacttactg agcgttcagg tcgacctcag      900
ggcaaacatt ataggaacga ataa                                              924
```

<210> SEQ ID NO 6
<211> LENGTH: 993
<212> TYPE: DNA
<213> ORGANISM: Unknown
<220> FEATURE:
<223> OTHER INFORMATION: Originating from a metagenomic clone library
      without identification of the source organism.

<400> SEQUENCE: 6

```
ctattgggtc ttcgagacta tgcagcaaga actcatctta gtattggaac agcggtagat       60
gtaaatgctc tttctaatga agaacaatat cagctggtgg tggtcagaga attcaatagt      120
gttaccccag aaaatgtcat gaaatgggat actattgagc ccatacgtgg tcagctaaat      180
tttgagccag cagatcagct cgtagatttt gcacggcggc atggtcagat agtgagagag      240
cacacactcg tctggcataa ccaactgccc agctggttga caaatggtaa ctttaccaac      300
caggagctgg aggaaatact gcgacagcac atctatgatg ttgtaaggca tttcaagggc      360
aaggtgtatt cttgggacgt agtgaacgag cccctgaatg aagatggtac cctaagggat      420
agcatatggc ttagggctat tggtccggat tacatagcca aagctttcca atgggcgcac      480
gaggctgatc cacatgccaa actctacatc aatgactaca acattgagtg gatcgggcct      540
aagagcaatg gaatgtacga gctggtgaag agtctcaagg aagcaggtgt gcctatcgat      600
ggcgtgggat tcaaggaca tctcggcata cagtatggat ttcctgggga tattcaacag      660
aatattcaga gatttgctga tctgggattg gatgtggctc tgtctgaggt ggatgtgcgc      720
atgattctac ctgttaccca agagaaactt gctacacagg ctgagtatta ccgtcgactt      780
atggatgctt gtctgaatgt acgacgatgc gtatctttca cagtgtgggg attcaccgat      840
gctcactcat gggtacccgg attcttccaa ggacaaggtg cggccactat atttgatgag      900
aattatcagc cgaaaccagc gtattttgct ttgaaggat aacttactga gcgttcaggt       960
cgacctcagg gcaaacatta taggaacgaa taa                                  993
```

<210> SEQ ID NO 7
<211> LENGTH: 996
<212> TYPE: DNA
<213> ORGANISM: Unknown
<220> FEATURE:
<223> OTHER INFORMATION: Originating from a metagenomic clone library
      without identification of the source organism.

<400> SEQUENCE: 7

```
aagagattgg gactgagaga ttacgctgct agaacccact tgtctatcgg aaccgccgtt       60
gacgttaacg ctctgtctaa cgaggaacag taccagctgg ttgttgtgag agagttcaac      120
tctgttaccc cagagaacgt gatgaagtgg gacaccatcg agccaattag aggacagctg      180
aactttgagc cagctgacca gttggttgac ttcgctagaa gacacggaca gattgtgaga      240
gagcacaccc ttgtttggca caaccagctg ccatcttggt tgaccaacgg caacttcacc      300
aaccaggaac tggaagagat tctgagacag cacatctacg acgttgtgag acacttcaag      360
ggcaaggtgt actcttggga cgttgttaac gagccattga cgaggacgg tactctgaga      420 gactctatct ggctgagagc tatcggtcca gactacatcg ctaaggcttt tcagtgggct      480
cacgaagctg atccacacgc caagctgtac atcaacgact acaacatcga gtggatcggt      540
```

-continued

```
ccaaagtcta acggaatgta cgagctggtg aagtctttga aagaggccgg cgttcctatt        600
gatggtgttg gtttccaggg tcacctgggt attcagtacg gtttcccagg tgacatccag        660
cagaacatcc agagatttgc tgacctggga ctggatgttg ctttgtctga agtggatgtg        720
agaatgatcc tgccagtgac ccaggaaaag ttggctactc aggccgagta ctatagaaga        780
ttgatggacg cctgcctgaa tgttagaaga tgcgtgtctt tcactgtgtg gggtttact         840 gacgctcact cttgggttcc aggattctt cagggtcaag gtgccgctac tatcttcgac         900
gagaactacc agccaaagcc agcttacttt gccttgaagg acgagttgac cgagagatct        960
ggtagaccac agggaaagca ctacagaaac gagtaa                                   996

<210> SEQ ID NO 8
<211> LENGTH: 1245
<212> TYPE: DNA
<213> ORGANISM: Unknown
<220> FEATURE:
<223> OTHER INFORMATION: Originating from a metagenomic clone library
      without identification of the source organism.

<400> SEQUENCE: 8
atgagatttc cttcaatttt tactgcagtt ttattcgcag catcctccgc attagctgct        60
ccagtcaaca ctacaacaga agatgaaacg gcacaaattc cggctgaagc tgtcatcggt       120
tactcagatt tagaagggga tttcgatgtt gctgttttgc catttccaa cagcacaaat        180 aacgggttat tgtttataaa tactactatt gccagcattg ctgctaaaga agaaggggta       240
agcttggata agagattggg actgagagat tacgctgcta gaacccactt gtctatcgga       300
accgccgttg acgttaacgc tctgtctaac gaggaacagt accagctggt tgttgtgaga       360
gagttcaact ctgttacccc agagaacgtg atgaagtggg acaccatcga gccaattaga       420
ggacagctga actttgagcc agctgaccag ttggttgact tcgctagaag acacggacag       480
attgtgagag agcacaccct tgtttggcac aaccagctgc catcttggtt gaccaacggc       540
aacttcacca accaggaact ggaagagatt ctgagacagc acatctacga cgttgtgaga       600
cacttcaagg gcaaggtgta ctcttgggac gttgttaacg agccattgaa cgaggacggt       660
actctgagag actctatctg gctgagagct atcggtccag actacatcgc taaggctttt       720
cagtgggctc acgaagctga tccacacgcc aagctgtaca tcaacgacta caacatcgag       780
tggatcggtc caaagtctaa cggaatgtac gagctggtga agtctttgaa agaggccggc       840
gttcctattg atggtgttgg tttccagggt cacctgggta ttcagtacgg tttcccaggt       900
gacatccagc agaacatcca gagatttgct gacctggac tggatgttgc tttgtctgaa        960
gtggatgtga gaatgatcct gccagtgacc caggaaaagt tggctactca ggccgagtac      1020
tatagaagat tgatggacgc ctgcctgaat gttagaagat gcgtgtcttt cactgtgtgg      1080
ggttttactg acgctcactc ttgggttcca ggattcttc agggtcaagg tgccgctact       1140
atcttcgacg agaactacca gccaaagcca gcttactttg ccttgaagga cgagttgacc      1200
gagagatctg gtagaccaca gggaaagcac tacagaaacg agtaa                      1245
```

THERMOSTABLE XYLANASE FOR THE SELECTIVE HYDROLYSIS OF PENTOSE-CONTAINING POLYSACCHARIDES

RELATED APPLICATIONS

This application is a 35 U.S.C. §371 national stage filing of International Application No. PCT/EP2010/069736, filed Dec. 15, 2010, which is related and claims priority to EP Application Serial No.: 09 180 210.8, filed Dec. 21, 2009. The entire contents of these applications are explicitly incorporated herein by reference.

SEQUENCE LISTING

The instant application contains a Sequence Listing which has been submitted in ASCII format via EFS-Web and is hereby incorporated by reference in its entirety. Said ASCII copy, created on Dec. 17, 2012, is named 117814_03601_SeqListing.txt and is 18,955 bytes in size.

BACKGROUND OF THE INVENTION

Hemicelluloses and particularly xylan-containing polysaccharides are a valuable source for the production of monosaccharides that can be converted into biofuels, industrial platform chemicals, consumer products, food and feed additives. Due to the heterogeneous chemical structure of this material its degradation requires a series of physicochemical and/or enzymatic treatment steps. Processes that enable an effective and selective hydrolysis of pentose-containing polysaccharides are highly desirable.

An important source of pentoses from biomass is xylan. Xylan constitutes about 15-25% of lignocellulosic biomass and up to 70% of other feedstocks such as oat spealts. Xylans represent one of the major components of plant cell walls and are abundantly found in agricultural waste products, e.g. wheat straw, corn stover, corn cobs, and cotton seed. Xylans consist of xylose monomeric subunits linked by β-1-4-glycosidic bonds in a complex polymer with various other components such as arabinose, glucuronic acid, methylglucuronic acid, and acetyl groups. In cereals, xylans frequently contain side chains of α-1,2- and/or α-1,3-linked L-arabinofuranoside. These substituted xylans are commonly referred to as arabinoxylans. Xylans that are substituted with glucose are referred to as glucoxylans. Also mixed forms of these xylans exist.

Xylanases (β-1,3- or β-1,4-xylan xylohydrolase; E.C. 3.2.1.8) are xylanolytic enzymes that depolymerize xylans, arabinoxylan, and/or other xylose-containing polysaccharides. Endo-xylanases (e.g. endo-β-1,4-xylanase) hydrolyze the internal β-glycosidic linkages in xylan, arabinoxylan, and/or other xylose-containing polysaccharides to produce smaller molecular weight xylo-oligomers or xylose monomers.

Major industrial applications of xylanases today are in the pulp and paper industry to improve the bleachability of pulps and to produce xylose as basis for the sweetener xylitol. Furthermore, xylanases can be used in food and feed compositions which contain cereals (e.g. barley, wheat, maize, rye, triticale, or oats) or cereal by-products that are rich in xylans, arabinoxylans and/or glucoxylans. Addition of xylanases to animal feed or baking products improves the break-down of plant cell walls which leads to better utilization of plant nutrients and/or prolonged bread freshness, respectively. In feed compositions xylanase addition leads to improved animal growth rate and feed conversion. Additionally, the viscosity of feed compositions containing xylan can be reduced by xylanase leading to better acceptability and adsorption.

Despite the relatively high number of known fungal and bacterial xylanases, the number of xylanases which are industrially applicable remains limited. This is mainly due to physical process conditions, such as high temperature and low pH, as well as lack of substrate and/or product selectivity. Such drawbacks limit the use of xylanases.

Typical fungal xylanases are inefficient at temperatures higher than 60° C. and they generate a broad spectrum of sugar products containing mixtures of hexoses and pentoses (Saha, B. C. (2003) Hemicellulose bioconversion. J. Ind. Microbiol. Biotechnol. 30:279-291). The lack of product specificity and the rapid deactivation of these enzymes at process temperatures>60° C. limits their application in industrial applications. Higher product specificity and operating temperatures would, however, result in simplified purification procedures and faster product generation, leading to overall process intensification and cost reduction.

While typical fungal xylanase preparations operate between pH 3.5-6.0, they are rapidly deactivated under process conditions outside this pH range (Kulkani, N., Shendye, A., Rao, M. (1999) Molecular and biotechnological aspects of xylanases FEMS Microbiology Reviews 23:411-456; Savitha S, Sadhasivam S, Swaminathan K. Application of *Aspergillus fumigatus* xylanase for quality improvement of waste paper pulp. Bull Environ Contam Toxicol. 2007 April; 78(3-4):217-21). However, for food and feed applications it is desirable that xylanases are stable and/or operate over a broad pH range.

An additional preferable feature is resistance to proteolytic hydrolysis, which would result in higher process stability. Available xylanase are either not resistant to hydrolysis or lack the desired product specifity or temperature stability (Mendicuti Castro L P, Trejo-Aguilar B A, Aguilar Osorio G. Thermostable xylanases produced at 37 degrees C. and 45 degrees C. by a thermotolerant *Aspergillus* strain. FEMS Microbiol Lett. 1997 Jan. 1; 146(1):97-102; Li N, Yang P, Wang Y, Luo H, Meng K, Wu N, Fan Y, Yao B. (2008) Cloning, expression, and characterization of protease-resistant xylanase from *Streptomyces fradiae* var. k11. J Microbiol Biotechnol. 18(3):410-416).

Typically, fungal xylanases have a temperature optimum of about 50° C. and a lower pH optimum than bacterial xylanases. A typical example of a fungal xylanase was isolated from *Trichoderma longibrachiatum* (Xyl1, Mr: 20 Kda, pI~5.5, 4). The enzyme has temperature and pH optima around 50° C. and pH 4.5, respectively. The xylanase is stable over a pH range from 3-8 and is deactivated above 55° C. as expected for fungal enzymes. The enzyme preferentially cleaves xylose units from either linear xylan or branched hemicellulose polymers. Like other fungal xylanases it also has a rather broad substrate specificity, leading to significant cellulase and arabinase side activities. Fungal xylanases that have been modified to increase thermostability are disclosed in WO 02/18561A2.

In contrast to fungal xylanase, several xylanases from bacteria have a temperature optimum in the range of 50 to 80° C. One example is a thermostable xylanase from *Thermobifida* (*Thermomonospora*) *fusca* (Mr: 22 kDa, pI~5) which operates in the pH range between 5-8 and at temperatures of 50-75° C. Other thermostable xylanases are described in WO 03/106654A2

However, for industrial applications highly efficient xylanases with enhanced thermostability are desirable.

SUMMARY OF THE INVENTION

The present invention discloses novel polypeptides having xylanase activity which are characterized by high thermostability. Preferably, the polypeptide according to the present invention maintains at least 80%, more preferably more than 90% of its xylanase activity after 72 hours incubation at 70° C. in 50 mM phosphate buffer pH 5.0.

The present invention further provides a nucleic acid encoding the polypeptide according to the present invention. In a preferred embodiment, a nucleic acid encoding a polypeptide having an amino acid sequence with at least 70% sequence identity, preferably 90% sequence identity, to the SEQ ID No: 1 or SEQ ID NO:3 is provided.

The present invention further provides a vector comprising a nucleic acid of the present invention.

The present invention further provides a host cell transformed with a vector comprising a nucleic acid of the present invention.

The invention also provides methods of preparing xylanases, including substrate-selective and thermotolerant xylanases, comprising the steps of obtaining a host cell of the present invention, which has been transformed with a vector of the present invention, preferably with a vector comprising a nucleic acid encoding a polypeptide having an amino acid sequence with at least 70% sequence identity to the SEQ ID No: 1, cultivating the host cell under conditions under which the xylanase protein encoded by said nucleic acid is expressed and recovering the xylanase protein.

The present invention further provides a composition comprising a polypeptide according to the present invention and a cellulase.

The invention also discloses the use of a polypeptide according to the present invention and of the composition according to the present invention for the enzymatic degradation of lignocellulosic biomass.

DEFINITIONS

Figure 1:
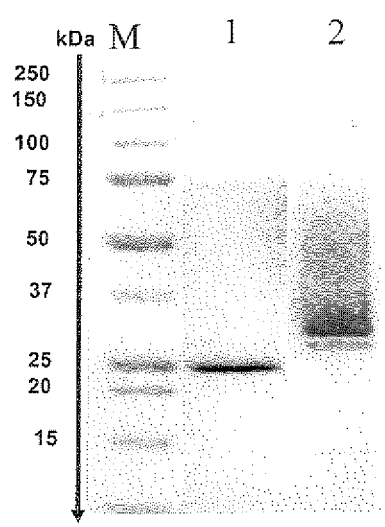
FIG. 1: Recombinant expression of Xyl7A, Purity of xylanase preparations, SDS-PAGE, Coomassie-stained, M=Marker; 1=Xyl 1 (control); 2=Xyl7A

The term "xylanase" is defined herein as a β-1,3- or β-1, 4-xylan xylohydrolase (E.C. 3.2.1.8), which catalyzes the hydrolysis of β-1,3- or β-1,4-xylosidic linkages with the release of smaller molecular weight xylo-oligomers or xylose monomers.

The term "mutations" shall comprise any kind of nucleotide sequence modification including insertions, deletions, points mutations, inversions, or combinations thereof.

In this invention, the term "fermentive production process" is defined as any production process, which comprises the cultivation of microorganisms to produce one or more desired products. Possible examples of such processes are the fermentative production of chemicals such as ethanol, propanol, propandiol, glycerol, butanol, butandiol, and organic acids, or any combination thereof.

The term "monomeric or oligomeric building blocks" means monomeric or oligomeric products, which are released from the raw polymeric feedstock using an enzyme system. "Oligomeric" shall include compounds with two or more monomeric units.

"Yeast" shall herein refer to all lower eukaryotic organisms showing a unicellular vegetative state in their life cycle. The term "yeast" in the context of yeast expression systems means organisms of the genus *Candida, Kluyveromyces, Saccharomyces, Schizosaccharomyces, Pichia, Hansenula*, and *Yarrowia*.

The terms "fungi" and "fungal" refer to *Basidiomycetes, Oomycetes, Zygomycetes, Chythridiomycetes*, and *Ascomycetes*. In particular, the term refers to organisms of the genus *Aspergillus, Trichoderma*, and *Penicillium*.

The term "marker genes" refers to genes that impart a distinct phenotype to cells expressing the marker gene and thus allow such transformed cells to be distinguished from cells that do not have the marker. Such genes may encode either a selectable or screenable marker.

"Thermostability" herein refers to an enzymatic property where the fraction of still active enzyme after an incubation period is compared to the fraction of still active enzyme remaining from a reference enzyme under the same conditions.

The term "selectivity" with regard to xylanases refers to substrate acceptability and product spectrum. Enzyme hydrolysis with low selectivity results in mixtures of sugars, containing one or more hexoses and/or one or more pentoses, after hydrolysis of lignocellulosic biomass. Such mixtures are difficult to separate and complicate the down-stream processing of the reaction products.

"Protease stability" and "Resistance to protease hydrolysis" herein refers to the property of an enzyme of retaining enzyme activity under the influence of a protease, e.g. trypsin or chymotrypsin. The protease stability may be determined by measuring the enzyme activity after the incubation of the enzyme in the presence of a protease. A detailed method of determining the protease stability is described in Example 8

DETAILED DESCRIPTION OF INVENTION

The Polypeptide According to the Present Invention

Thermostability

The present invention discloses novel polypeptides having xylanase activity, which are characterized by high thermostability. Preferably, the polypeptide according to the present invention maintains at least 80%, more preferably more than 90% of its xylanase activity after 72 hours incubation in 50 mM phosphate buffer at 70° C.

A detailed method of determining thermostability is described in Example 7.

The polypeptide of the present invention furthermore preferably shows one or more of the following properties:

Optimum Temperature

Activity at elevated temperatures of the polypeptide of the present invention is determined by measuring xylan hydrolysis at various temperatures for a certain amount of time under the following conditions: pH 5, 2% w/w dry weight substrate concentration, enzyme:substrate ratio (E/S) of 1% w/w dry weight. A detailed method of determining thermostability is described in Example 5.

The polypeptide according to the present invention preferably shows an optimum xylanase activity in the temperature range of 45-78° C. Most preferably, the polypeptide according to the present invention shows an optimum xylanase activity in the temperature range of 65-75° C.

pH Profile

The polypeptide according to the present invention is preferably characterized by a wide pH activity profile. More preferably, it is active over a pH range from 3.5-6.0. Most preferably, the polypeptide shows optimum xylanase activity in the pH range of 5-6.

A detailed method of determining pH profile is described in Example 6.

Resistance to Protease Hydrolysis

The polypeptide according to the present invention preferably shows high protease stability. More preferably, the polypeptide maintains at least 80%, most preferably 90%, of its xylanase activity after having been subjected to trypsin at pH 7.8 and 50° C. for 1 hour.

A detailed method of determining resistance to protease hydrolysis is described in Example 8.

Suitability for Large-Scale Production

The polypeptide according to the present invention is preferably characterized by high expression and optionally high secretion rates from various microorganisms, in particular by secretion from fungal and/or yeast hosts. More preferably, the polypeptide according to the present invention is expressed and secreted at a level of more than 100 mg/l, even more preferably at a level of 1 g/l into the supernatant after introduction of a promoter functionally linked to a nucleic acid encoding the polypeptide into a suitable expression host.

A suitable expression host is preferably yeast, in particular a methylotrophic yeast. Particularly suitable yeast expression hosts are *Hansenula polymorpha, Pichia angusta*, and *Pichia pastoris*. Expression in a Yeast is described in Example 1.

Another suitable expression host is a bacterium. Particularly suitable expression hosts are *Bacillus subtilis* and *Escherichia coli*.

Another suitable expression host is a fungus. Particularly suitable expression hosts are *Aspergillus niger, Penicilium*, and *Trichoderma reesei*.

Detailed methods of determining expressibility, i.e yield of a secreted protein and/or enzyme in the supernatant of a culture or yield of intracellular protein/enzyme after disrupting the cells are described in the Examples 1 and 2.

Substrate Selectivity

The polypeptide according to the present invention preferably carries out hydrolysis of pentose-containing polysaccharides in a substrate-selective manner. In particular, the polypeptide according to the present invention is characterized by high selectivity towards hydrolysis of xylose-containing polysaccharides and the releases of oligoxylose or xylose monomers. Most preferably, the polypeptide according to the present invention yields xylose and glucose in a weight ratio of at least 10:1 when subjecting wheat straw to the polypeptide at pH 5 and 45° C.

A detailed method of determining substrate selectivity is described in Example 4.

Protein Size and Charge

The polypeptide according to the present invention preferably comprises a signal peptide which is cleaved off during secretion into the supernatant.

The polypeptide according to the present invention preferably comprises a polypeptide chain of more than 250 amino acids. More preferably, the length is between 290 and 370 amino acids, even more preferably between 310 and 350 amino acids. Most preferably the polypeptide comprises between 330 and 334 amino acid residues.

The polypeptide according to the present invention preferably has a molecular weight of more than 30 kD. More preferably, the size is between 32 and 45 kD, even more preferably between 34.5 and 42.5 kD. Most preferably the polypeptide has a size between 38 and 39 kD. A particularly suitable size is 38.5 kD.

The polypeptide according to the present invention preferably has a pI between 4 and 7, even more preferably between 5 and 6. Most preferably the polypeptide has a pI between 5.4 and 5.6 kD. A particularly suitable pI is 5.5.

Examples for protein sizes and suitable signal sequences are described in Example 1 and corresponding sequences SEQ ID NO:1-4.

The polypeptide according to the present invention may exhibit any one of the properties thermostability, pH stability, resistance to protease hydrolysis, suitability for large-scale production and substrate selectivity described above. Preferably, the polypeptide according to the present invention exhibits more than one of these properties, wherein any combination of the properties is possible. Most preferably, the polypeptide according to the present invention exhibits all of these properties.

The present invention also provides polypeptides having at least 70% identity, preferably at least 75%, 80%, 85%, 90%, or 95%, to SEQ ID NO: 1 or SEQ ID NO: 3.

In a preferred embodiment, the polypeptide according to the present invention has the sequence as defined by SEQ ID NO:1 or SEQ ID NO:3, or a sequence as defined by SEQ ID NO:1 or SEQ ID NO:3, wherein any 1 to 30 amino acid residues are substituted, deleted, or inserted. Any 1 to 30 amino acid residues in the sense of this application means that 1 to 30 amino acid residues, irrespective of their position within the polypeptide, are substituted, deleted, or inserted.

In particular, the present invention provides the novel polypeptides Xyl7A (SEQ ID NO: 1) and Xyl7AY (SEQ ID NO: 3). Furthermore, polypeptides (SEQ ID NO: 2) and Xyl7AY-L (SEQ ID NO: 4) comprising the respective mature proteins as well as N-terminal signal peptides are disclosed. The novel xylanase sequences orginate from a metagenomic clone library without identification of the source organism.

The disclosed xylanase sequence was identified by combining sequencing approaches and functional characterization of a variety of potential xylanase enzymes. Methods and instrumentation for carrying out such screening strategies are known to those skilled in the art and are well documented in the literature.

The novel xylanase sequences have been analyzed for sequence similarity, conserved domains, and physical protein characteristics using standard bioinformatic tools. Sequence analysis of the novel protein sequence indicated a theoretical molecular mass of 38 kDa and a pI value of 5.4.

On nucleotide level the Xyl7A sequence showed the highest sequence identity (50%) to a xylanase of the GH 10 class from *Meripilus giganteus*. The nearest characterized protein was a GH 10 endoxylanase from *Thermomonospora (Thermobifida) fusca* with an identity of 37% to Xyl7A on the protein level. Analysis of Xyl7A conserved domains using the CDART tool indicated that the protein contains a single catalytic domain which is on amino acid level most closely (56% identity) related to an endoxylanase of the GH 10 family.

The GH10 xylanase family is known to include certain thermostable enzymes with temperature optima between 50-70° C. It is also known that xylanases of the GH10 and 11 family are able to hydrolyse xylan heteropolymers, which besides xylose may also contain varying degrees of glucose and arabinose residues.

Preferably, the disclosed enzymes show a particularly high thermostability above 70° C. when incubated on various substrates, a broad operational pH range between 4-7 and a pronounced stability to proteases. The particular combination of said aspects make the disclosed xylanases valuable for an array of industrial applications.

The present invention also provides fusion proteins of the polypeptide of the present invention with other protein sequences. Such sequences can represent catalytically active proteins, binding proteins, proteins influencing aspects of the cellular expression or sequences influencing chemical, catalytic, biological or physical properties of the fused target protein, or being without particular effect. The fusions also include those containing only parts of the target sequence, wherein this part contributes to the enzymatic activity of the fusion protein. Of special interest among the fusions with catalytically active proteins are those with proteins selected from the group of carbohydrate-modifying enzymes. Of special interest among the fusions with binding proteins are those made with binding modules from carbohydrate-modifying enzymes. It is well known that such fusions can beneficially influence the enzymatic and physical properties of the fused parts, especially those of the target protein.

In a particular embodiment of the present invention the claimed target sequence of Xyl7A is fused with a carbohydrate-binding module with special affinity to xylan or other polymeric sugars found in hemicellulose.

In a more preferred embodiment of the present invention the fusion partners of the Xyl7A sequence are selected from carbohydrate-binding module (CBM) sequences from the classes 13, 15, 22, 31, 35, 36 or 37.

Non limiting examples of CBM fusion partners for the claimed target sequence selected from class 13 are the xylan-binding modules of *Streptomyces lividans* (Blast Entry no. AAC26525.1) and *Aspergillus fumigatus* Af293 (Blast Entry no. EAL91233.1).

Particularly preferred fusion partners of the Xyl7A target sequence are the CBMs of *Thermobifida fusca* (Blast Entry no. AAZ55678.1) and *Teredinibacter turnerae* T7901 (Blast Entry no. ACS93528.1).

Non limiting examples of CBM fusion partners for the claimed Xyl7A target sequence selected from class 22 are the xylan-binding modules of *Paenibacillus barcinonensis* (Blast Entry no. CAA07173.1), *Thermoanaerobacterium saccharolyticum* (Blast Entry no. AAC43719.1) or *Xylanimicrobium pachnodae* (Blast Entry no. AAD54768.1), *Cellulomonas fimi* (Blast Entry no. CAA90745.1) or *Caldicellulosiruptor* sp. Rt69B.1 (Blast Entry no. AAB95326.1).

A non limiting example of a CBM fusion partner for the claimed target sequence selected from class 36 is the xylan-binding modules of *Clostridium phytofermentans* ISDg (Blast Entry no. ABX42059.1).

A non limiting example of a CBM fusion partner for the claimed target sequence selected from class 37 is the xylan-binding modules of *Ruminococcus albus* 8 (Blast Entry no. AAT48119.1).

Nucleic Acids, Vectors, Host Cells

Furthermore, nucleotide sequences encoding polypeptides according to the present invention, expression cassettes, constructs and vectors comprising these nucleotide sequences and recombinant host cells transformed with said vectors are disclosed.

The present invention provides a nucleic acid encoding the polypeptide according to the present invention. In a preferred embodiment, a nucleic acid encoding a polypeptide having an amino acid sequence with at least 70% sequence identity, preferably 90% sequence identity, to the SEQ ID No: 1 or SEQ ID NO: 3 is provided.

In a further preferred embodiment, the nucleic acid encodes a polypeptide according to the present invention having the sequence as defined by SEQ ID NO:1 or SEQ ID NO:3, or a sequence as defined by SEQ ID NO:1 or SEQ ID NO:3, wherein any 1 to 30 amino acid residues are substituted, deleted, or inserted.

Furthermore, DNA sequences encoding Xyl7A (SEQ ID NO: 5), Xyl7A-L (SEQ ID NO: 6), Xyl7AY (SEQ ID NO: 7) and Xyl7AY-L (SEQ ID NO: 8) are disclosed. The present invention further provides DNA sequences having at least 70%, more preferably at least 75%, 80%, 85%, 90% or 95% identity to SEQ ID NO: 5 or SEQ ID NO: 7.

Mutations may be introduced into the nucleotide sequence of this invention. Mutations within the coding region modify the amino acid sequence, the protein structure and/or the activity of the xylanase.

The present invention further provides a vector comprising a nucleic acid of the present invention. Preferably, the nucleic acid encodes a polypeptide having an amino acid sequence with at least 70% sequence identity, more preferably at least 75%, 80%, 85%, 90% or 95% sequence identity, to the SEQ ID No:1 or SEQ ID No:3.

In another preferred embodiment, the vector according to the present invention comprises a nucleic acid encoding a polypeptide according to the present invention having the sequence as defined by SEQ ID NO:1 or SEQ ID NO:3, or a sequence as defined by SEQ ID NO:1 or SEQ ID NO:3, wherein any 1 to 30 amino acid residues are substituted, deleted, or inserted.

In another preferred embodiment, the vector according to the present invention comprises the nucleic acid of SEQ ID NO: 5, SEQ ID NO: 6, SEQ ID NO: 7 or SEQ ID NO: 8, or a nucleic acid sequence having at least 70%, more preferably at least 75%, 80%, 85%, 90% or 95% identity to SEQ ID NO: 5 or SEQ ID NO: 7.

The vector according to the present invention may be episomally maintained in the host cell or integrated into the chromosome of the host.

Examples for known vectors are derivatives of bacterial plasmids, yeast plasmids, centromer based linear DNA, constructs of viral origin like SV40, phage DNA, baculovirus, vaccinia, adenovirus, fowl pox virus, and pseudorabies as well as vectors derived from combinations of plasmids and phage or viral DNA.

A suitable expression vector according to the present invention may comprise one or more genetic elements representing promoter sequences, transcription initiation sites, elements for the initiation of translation, and functional elements for protein export that are translationally coupled to the nucleic acid according to the present invention.

A vector of the present invention may encode more than one polypeptide including more than one xylanase or may encode a fusion polypeptide comprising the xylanase of the invention.

The present invention further provides a host cell transformed with a vector according to the present invention. The host cell according to the present invention may be used for recombinant protein production or for metabolic transformation of xylose containing substrates to preferred metabolites.

The recombinant host cells according to the present invention can be bacteria, yeast, or fungal cells. In particular the host cell is selected from the group comprised of bacteria, comprising *Escherichia, Klebsielia, Pseudomonas, Lactobacillus, Bacillus, Streptomyces*; yeasts comprising *Saccharomyces, Kluyveromyces, Schizosaccharomyces, Candida, Yarrowia, Pichia, Hansenula*; and fungi comprising *Aspergillus, Penicillium*, or *Trichoderma*. Preferably, the host cell is selected from the group comprised of *Escherichia coli, Bacillus subtilis, Bacillus licheniformis, Bacillus amyloliquefaciens, Bacillus megaterium, Saccharomyces cerevisiae, Schizosaccharomyces pombe, Pichia pastoris, Pichia angusta. Aspergillus niger, Aspergillus oryzae*, or *Trichoderma reesei*.

In a preferred embodiment of the invention, the host cell is selected from the group consisting of *Saccharomyces cerevisiae, Schizosaccharomyces pombe, Kluyveromyces lactis, Pichia pastoris, Pichia angusta, Hansenula polymorpha, Aspergillus niger, Trichoderma reesei, Penicillium* sp. In another preferred embodiment of the invention, the host cell is a methylotrophic yeast and is selected from the group consisting of *Pichia pastoris, Pichia angusta, Hansenula polymorpha*. Most preferably the host cell of the present invention is *Pichia* spp. or *Hansenula* spp.

A recombinant host cell according to the present invention may comprise one or more vectors of the present invention.

A further aspect of the invention includes expression cassettes allowing the expression of the polypeptide according to the present invention, particularly of the Xyl7A protein, in-vivo or in-vitro.

An expression cassette preferably comprises a promoter region upstream to the coding sequence of the gene encoding the polypeptide according to the present invention, preferably the Xyl7A gene, sites involved in the formation of the translation initiation complex, optional regulatory sequence elements such as repressor binding or enhancer sites and optional a transcription termination sequence. Promoters may contain sequences allowing the binding of protein factors required for the transcription of coding sequence or functional mRNA. Furthermore sequences of the promoter may influence the effectiveness of transcription under a given physiological or chemical condition. A promoter may comprise elements in close proximity to the coding region or situated in more distant regions acting as enhancers. Promoters may be of prokaryotic, eukaryotic, archeal or viral origin or synthetic in nature. Preferred promoters include bacterial promoters of beta galactosidase (lacZ) gene, the tryptophans operon pomoter (trp), tetracycline resistance gene promoter (tet), the araBAD promoter, virus-derived promoters T7, T3, PL or PR. Preferred promoters for the expression in yeast include glyceraldehyde phosphate dehydrogenase (GAP) promoter, hexokinase promoter, alcohol dehydrogenase ADE2 promoter, GAL1, GAL10, TEF and promoters of the methanol metabolic pathway of methylotrophic yeasts such as AOXI, MOXI or FMDH, as well as the copper-inducible CUP1 promoter. Preferred promoters for the expression in filamentous fungi include those from the celluloytic enzymes, such as CBHI, CBIII, or EGI or II, α-amylase, glucoamylase, phosphoglycerate kinase (pgk), and any promoter of genes of the glycolytic pathway.

Expression levels of a gene encoding the polypeptide according to the present invention can be increased by adjustment of the copy-number of the gene introduced into the host cells, preferably resulting in more than single copies of the gene. For optimized expression of the gene, the promoter can be regulated, either by induction following the addition of a chemical inducer by adjustment of a physical parameter. Examples for inducible systems include tetracycline repressor system, Lac repressor system (Baneyx, P. (1999) Recombinant protein expression in *Escherichia coli*; Current Opinion in Biotechnology 10:411-422), copper-inducible systems (Hottiger, T., Fürst, P., Pohlig, G, Heim, J. (2004) Physiological characterization of the yeast etallothionein (CUP1) promoter, and consequences of overexpressing its transcriptional activator, ACE1, Yeast 10:283-296), methanol inducible AOXI systems (Cereghino, Cregg, J. M. (2000) Heterologous protein expression in the methylotrophic yeast *Pichia pastoris* FEMS Microbiology Reviews 24:45-66) or the temperature inducible λPL promoter. Alternatively, de-repression of the promoter by reaching a suitable physiological state in the culture can be a useful strategy (Promoter of PhoA, Trp, Adh2, Fmdh, CBHI (Price, V., Taylor, W. E., Clevenger, W., Worthington, M., Young, E. T. (1990) Expression of heterologous proteins in *Saccharomyces cerevisiae* using the ADH2 promoter Methods Enzymol. 185:308-318; Hollenberg, C. P., Janowicz, Z. (1995) DNA-molecules coding for FMDH control regions and structural gene for a protein having FMDH-activity and their use thereof, U.S. Pat. No. 5,389,525)). Application of strong stationary promoters might be preferable in other situations (GAP, TEF).

A translational coupling of signal peptide sequences can be used for the directing of the expressed polypeptide according to the present invention to cellular compartments, organelles or the export from the host cell. Signal sequences are well known in the art, Examples are leader sequences for the periplasmatic targeting from OmpA, OmpT, PelB, PhoA, glucanase or β-lactamase. Signal peptides for secretion of the proteins can be found among naturally secreted carbohydrate modifying enzymes, namely leaders from coding sequences of celloiohydrolaseI or II, endogiucanases, amyE or signal peptides of the *S. cerevisiae* Mfα or chicken egg lysozyme.

The expression cassette may be placed in a vector or a vector construct according to the present invention which can be episomally maintained in the host cell or integrated into the chromosome of the host. Examples for known vectors are derivatives of bacterial plasmids, yeast plasmids, Centromer based linear DNA, constructs of viral origin like SV40, phage DNA, baculovirus, vaccinia, adenovirus, fowl pox virus, and pseudorabies as well as vectors derived from combinations of plasmids and phage or viral DNA. Integration of the expression cassette can be achieved by homologous recombination, transposition or by application of viral integration systems. Additionally the use of episomally maintained constructs as basis for the integration of the expression cassette copies into the chromosomal DNA is possible. Finally, any system leading to the replication of the expression cassette in the host cells is suitable as a vector-construct.

Preferred methods for the introduction of the expression cassette constructs into the host cell include transformation, transfection, conjugation and/or interbreeding. The transformation can be achieved by DNA transfer via electroporation, protoplast fusion, lipofection, ballistic bombardment, chemical transformation based on calcium chloride, PEG or manganese chloride. Further strategies include the application of viral particles. A further alternative is the application of naturally competent organisms as host cells.

Methods for further increasing the yield of the expressed protein include the co-expression of helper proteins involved in translation, trafficking of proteins, folding of proteins (e.g. Chaperones hsp70-family proteins, protein disulfide isomerise) or correct processing of the polypeptide (Kex, Ste proteases) and other events contributing to the cellular production of the protein.

After transformation of the host strain with a vector of the present invention and growth to an appropriate cell density, the selected inducible promoter is induced by temperature shift or chemical induction and cells cultured to yield the recombinant enzyme. Preferably, the polypeptide according to the present invention is produced with a signal peptide that directs the recombinant protein to be secreted from the host cell. Cells are then removed by centrifugation or filtration and the polypeptide-containing supernatant is retained.

Methods for Producing the Polypeptide According to the Present Invention

The invention also provides methods of preparing xylanases, including substrate-selective and thermotolerant xylanases, comprising the steps of obtaining a host cell, which has been transformed with a vector according to the present invention, cultivating the host cell under conditions under which the xylanase protein encoded by said nucleic acid is expressed and recovering the xylanase protein. In a preferred embodiment the vector comprises a nucleic acid encoding a polypeptide having an amino acid sequence with at least 70% sequence identity, more preferably at least 75%, 80%, 85%, 90% or 95%, to the SEQ ID No: 1 or SEQ ID No: 3.

In a preferred embodiment of the method according to the present invention the employed host cell comprises an expression cassette comprising a promoter which is operably linked to a nucleic acid molecule according to the present invention.

In a further preferred embodiment of the method according to the present invention the employed host cell is a yeast cell and the expressed polypeptide has a sequence as defined by SEQ ID No: 3 or a sequence as defined by SEQ ID No: 3, wherein any 1 to 30 amino acid residues are substituted, deleted, or inserted.

In a particular embodiment the enzyme is recovered and purified from the supernatant by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps are used as necessary.

In a particular embodiment the enzyme of the present invention is modified via glycosylation. In a particular embodiment glycosylated enzymes are improved in protein folding, conformational and thermostability stability, and resistance to proteolysis. In a particular embodiment the use of a glycosylated xylanase in animal feed helps protect the enzyme from thermal denaturation during feed pelleting and from proteolytic inactivation as it passes through the stomach of the animal, delivering active enzyme to the intestinal tract and site of action. For food processing applications where enzyme activity is desired only during processing and not in the final product a non-glycosylated, thermolabile, and proteolytic susceptible xylanase is preferred.

Composition

The present invention further provides a composition comprising a polypeptide according to the present invention and a cellulase.

Use of the Polypeptide and the Composition According to the Present Invention

The polypeptides of this invention may be employed for any purpose in which such enzyme activity is necessary or desired.

The xylanases described in this invention may be used alone or in combination with other hydrolytic, cellulolytic, hemicellulolytic and/or xylanolytic enzymes.

The invention particularly discloses the use of a polypeptide according to the present invention and of the composition according to the present invention for the enzymatic degradation of lignocellulosic biomass. A preferred embodiment of the present invention encompasses the use of a thermotolerant xylanase as a selective biocatalyst for the hydrolysis of specific polymeric biomass components such us lignocellulosic and hemicellulosic plant material.

The invention also discloses the use of a polypeptide according to the present invention in processes for the development of biofuels, platform chemicals and food and feed industries from complex substrates such as wheat straw.

In a specific embodiment of the invention the claimed polypeptide may be used to hydrolyse any substrate containing xylose oligomers (i.e. Xylotetraose, Xylopentaose, Xylohexanose) or polymers (i.e. Xylan or hemicellulose).

In a particular embodiment of the invention the polypeptide is used to hydrolyse pentose containing constitutents of complex biomass residues such as cereal straw, sugar cane bagasse, wood residues, corn cobs, peanut shells, fruit/vegetable waste, fruit pulp, soy hulls and cereal corn spelts.

In yet another embodiment of the invention the claimed polypeptide is used to hydrolyse pentose containing constituents of processed biomass substrates such as birch wood xylan, rye arabinoxylan, soy meal and cereal flour.

In a preferred embodiment of the invention the claimed polypeptide is applied together or in sequence with other enzyme systems, which may contribute in the decomposition of the above substrates. Non limiting examples of such enzyme systems are cellulases, arabinases, mannanases, pectinases, amylases, glucoamylases, glucosidases, glucanases, esterases, ligninases, laccases and oxidases.

In a preferred application of the invention the pentose constituents of polymeric biomass substrates are hydrolysed into their respective monomers and used as intermediates for the production of biofuels and renewable platform chemicals such as Xylitol, Ethanol and Furfural.

In a preferred embodiment of the invention, the polypeptide is employed for catalyzing the hydrolysis of xylan in animal feed. In another preferred embodiment, the polypeptide is employed for catalyzing the hydrolysis of xylan in food application, such as applied in the baking industry.

In a specific embodiment of the invention the polypeptide is used for the hydrolysis of polymeric and oligomeric xylose constitutents as found in the waste water of pulp and paper mills.

In yet another application of the invention the claimed polypeptide is used for hydrolysis of fruit pulp as practiced in the beverage industry.

EXAMPLES

The following examples, materials, and methods are for illustrative purposes only and are not to be construed as limiting the invention.

Example 1

Recombinant Expression of Xyl7A

For the functional expression of the target sequence the coding region is fused to a leader peptide by overlap extension PCR. For this purpose central oligo nucleotides are designed with 15 bases 5'-extensions identical to the complement of the first 15 nucleotides of the DNA strand each strand needs to be fused to. After separate amplification of the two fragments with outer and central primers the resulting fragments are mixed and the fused sequence is amplified with the outer primer pair. Fusions are made with the signal peptide of the mating factor alpha from *Saccharomyces cerevisiae*. Restriction endonuclease sites recognizing sequences placed on the 5'-extensions of the outer primers are used to ligate the PCR fragment into a compatible backbone of an expression plasmid. Digestion of PCR fragments with endonucleases, purification and analysis of DNA fragments by agarose gel electrophoresis, ligation of DNA fragments with T4-DNA ligase and transformation of *Escherichia coli* K12 Top10 cells was done essentially as described in Sambrook J, Russel D W. 2001. "Molecular Cloning: A Laboratory Manual," 3rd Ed., Cold Spring Harbor Press, Cold Spring Harbor, N.Y. The resulting expression construct carries the open reading frame of the translationally linked SPa sequence and the reading frame of the target sequence immediately downstream of the promoter region and upstream of the corresponding terminator region provided by the expression vector. Expression vectors used carry promoters of the metabolic genes from the methanol utilization pathway of methylotrophic yeast, the most prominent example being the promoter of the methanol oxidase gene.

The assembled expression vector is transformed in linear or circular form to the methylotrophic yeast strain *Hansenula polymorpha* (Gellissen G., *Hansenula Polymorpha*—Biology and Applications, (2002) Wiley-VCH Verlag GmbH Weinheim). The linear form was generated from the circular form by digestion of a unique restriction site situated in the promoter region. Transformants are selected for their antibiotic resistance marker (Zeocine or G418 resistance) after the electroporation event and are further grown under selective conditions to obtain strains showing highest specific activity with the pNP-b-d-xylopyranoside substrate when the culture is induced or has reached a de-repressed growth-state. Adjustment of antibiotic concentration during the transformation protocol is used to preferentially select for strains carrying multiple integrations of the Xyl7A expression construct. Expressibility is determined by measuring the protein concentration in the supernatant of cultures at several time intervals (0-72 hrs) according to the method by Bradford (Bradford, M M. (1976) A rapid and sensitive for the quantitation of microgram quantities of protein utilizing the principle of protein-dye binding. Analytical Biochemistry 72: 248-254), and by taking samples and analysing them by SDS page (FIG. 1).

Example 2

Xylanase Preparation

Xylanase (Xyl 1, GH 10, Source: *T. longibrachiatum* Cat. no.: E-XYTR2, Mr: 25 kDa Megazymes Inc., Ireland) was used as ammonium sulphate precipitates (total volume: 1 ml). Enzyme preparations were desalted and concentrated with 45 ml sodium acetate buffer (50 mM, pH 5) using 50 ml Amicon centrifugal ultrafiltration devices (10 kDa cut-off; Millipore, Maidstone, UK).

The recombinant xylanase Xyl7AY (Mr: 38 kDa, pI: 5.3) was expressed in yeast (*H. polymorpha*) as described above and secreted into the medium. For further testing the cell suspension was centrifuged at 150,000 g at 4° C. for 15 min to precipitate cell debris. The resulting clear supernatant was decanted and concentrated using a 400 ml Amicon stirred cell 8000 ultrafiltration device (Millipore, Frankfurt, Germany) equipped with a 10 kDa disk filter. The final protein preparation was concentrated to 15 ml containing approximately 80 mg protein. The protein concentration was determined using known methods (Bradford, M M. (1976) A rapid and sensitive for the quantitation of microgram quantities of protein utilizing the principle of protein-dye binding. Analytical Biochemistry 72: 248-254). Purity of the protein preparations was assessed using SDS-PAGE in combination with Coomassie Brilliant Blue G250 staining (FIG. 1). The experimental molecular mass as determined by SDS-PAGE was 39 kDa, which correlated well with theroretical mass (38 kDa) calculated from the amino acid sequence. Primary xylanase activities of each protein preparation were measured using the hydrolysis of p-NP-xylopyranoside as a substrate in analogy to standard protocols described in TAGUCHI, H., HAMASAKI, T., AKAMATSU, T., OKADA, H. (1996) A simple assay for xylanase using o-nitrophenyl-β-D-xylobioside. Bioscie. Biotechnol. Biochem. 60 (6), pp. 983-985.

Example 3

Preparation of Xylanase Substrates

Dry and milled samples of wheat straw (local agricultural produce) and oat spelt xylan (Sigma, Weilheim, Germany, Cat no: X0627) (2 g) were placed in a 50 ml test tube. The tube was then filled with 50 mM sodium acetate buffer (pH 5) up to 40 g (final concentration of 5% w/w). Rye arabinoxylan (Megazymes, Ireland, Cat no: P-RAXY) was supplied as white fine powder. For the preparation of the substrate stock solution 0.2 g was weighted into a 15 ml test tube. The tube was then filled with 50 mM sodium acetate buffer up to 4 g (final concentration of 5% w/w).

The complex chemical composition of each substrate (Table 1) was determined according to published methods (Sluiter A. B. Hames, R. Ruiz, C. Scarlata, J. Sluiter, D. Templeton, and D. Crocker, Determination of Structural Carbohydrates and Lignin in Biomass. Technical Report NREL/TP-510-42618 Revised April 2008).

TABLE 1

| Substrate Composition | | | | | | |
|---|---|---|---|---|---|---|
| Substrate | Cellulose (%) | Xylan (%) | Arabinan (%) | Uronic acids (%) | Total Lignin (%) | Ash (%) |
| Wheat straw | 35 | 24 | 3 | 2.5 | 23 | 8 |
| Oat spelt Xylan | 18 | 70 | 10 | 0 | 0 | 2 |
| Rye Arabino-xylan | 2 | 60 | 38 | 0 | 0 | 0 |

Example 4

Xylanase Activity and Product Selectivity

The hydrolytic activity and product selectivity of Xyl 1 from *T. longibrachiatum* was compared with recombinant xylanase Xyl7A. Both xylanases were used to hydrolyse the substrates wheat straw, rye arabinoxylan, and oat spelt xylan. Each of these substrates showed different contents of hexose and pentose sugars and different branching patterns of hemicellulose components.

Figure 2:
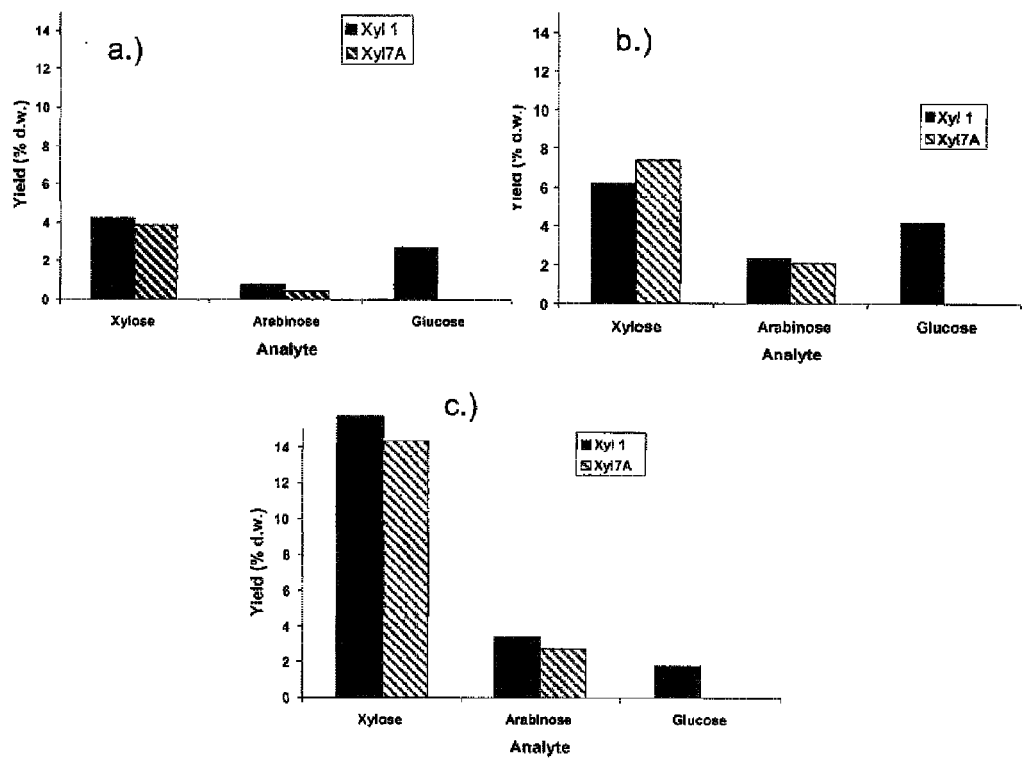
FIG. 2: Analysis of hydrolysis of a.) wheat straw, b.) oat spelt xylan, and c.) rye arabinoxylan using Xyl 1 (black bars) and Xyl7A (shaded bars).

All reactions were carried out in a total volume of 0.5 ml with a sodium acetate buffer (50 mM, pH 5). The standard reaction set-up consisted of substrate at 2% w/w dry weight and a enzyme:substrate ratio (E/S) of 1% w/w dry weight. The reactions were carried out at T=45° C. for 72 h. After the incubation the samples were centrifuged at 10,000 g for 15 min. The resulting supernatant was used to determine pentose and hexose composition using HPLC (Sluiter A. B. Hames, R. Ruiz, C. Scarlata, J. Sluiter, D. Templeton, and D. Crocker, Determination of Structural Carbohydrates and Lignin in Biomass. Technical Report NREL/TP-510-42618 Revised April 2008.) The results shown in FIG. 2 concentrate on changes in hydrolysis patterns of the major monomeric sugar components, Yields of hexose and pentose sugars are expressed in relation to their contribution to the particular biomass composition.

The relative hydrolytic activities of Xyl 1 and Xyl7A were comparable for each substrate set respectively. However, comparison of substrate selectivity surprisingly shows that, while Xyl 1 produced both hexose and pentose sugars, Xyl7A is significantly more selective towards the hydrolysis of pentose containing substrates. This leads to a significant process advantage as relatively pure product streams can be generated.

Example 5

Xylanase Activity and Temperature Optimum on Complex Polymeric Substrates

Enzyme activity at elevated temperature is desired in many biotechnological processes as it allows faster product turnover cycles at higher temperatures. It is therefore desirable to find enzyme activities that substantially retain their catalytic potential under high temperature conditions. The application of xylanases for the hydrolysis of complex biomass feedstocks is an important industrial application as the resulting monomeric sugars can be used as platform chemicals.

To compare the activity profiles of Xyl7A and Xyl 1 on complex polymeric substrates at elevated temperatures, enzymes were incubated over a wide range of temperatures with wheat straw as model substrate.

All reactions were carried out in a total volume of 0.5 ml with sodium acetate buffer (50 mM, pH 5). The reaction was carried out at 2% w/w dry weight substrate concentration and an enzyme:substrate ratio (E/S) of 1% w/w dry weight. The reactions were incubated at 50° C., 60° C. and 70° C. for 72 h under constant mixing (250 rpm). The analysis was done by HPLC as described previously (Sluiter A. B. Hames, R. Ruiz, C. Scarlata, J. Sluiter, D. Templeton, and D. Crocker, Determination of Structural Carbohydrates and Lignin in Biomass. Technical Report NREL/TP-510-42618 Revised April 2008). Yields calculated on the dry weight basis of xylan contained in the wheat straw substrate.

Figure 3:
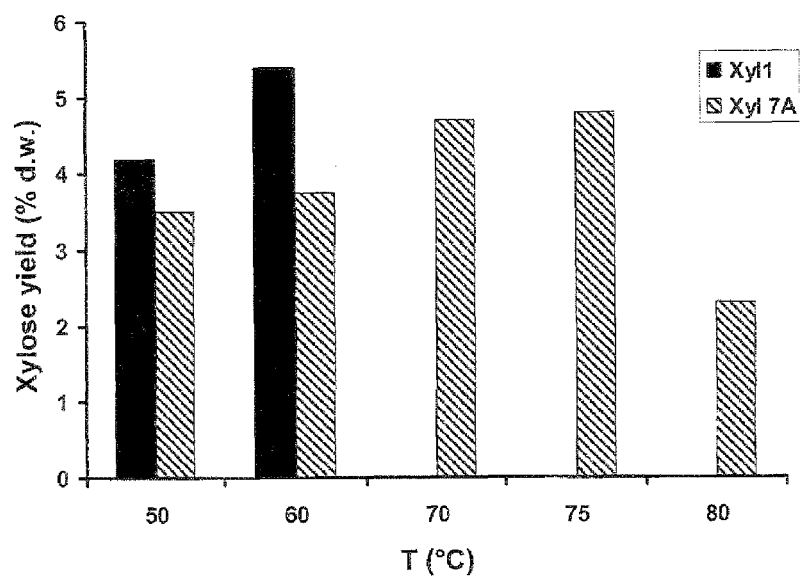
FIG. 3: Hydrolysis of wheat straw xylan by Xyl 1 and Xyl7A at different temperatures over 72 h reaction time. Activity is shown as xylose yield in % (w/w) of dry weight.

The temperature optimum of Xyl 1 and other xylanases derived from mesophilic fungi is reported as 60° C. (Berrie J G, Juge N. Factors affecting xylanase functionality in the degradation of arabinoxylans. Biotechnol Lett. 2008 July; 30(7):1139-50; Saha, B. C. (2003) Hemicellulose bioconversion. J. Ind. Microbiol. Biotechnol. 30., pp. 279-291; Kulkani, N., Shendye, A., Rao, M. (1999) Molecular and biotechnological aspects of xylanases. FEMS Microbiology Reviews 23, pp, 411-456 whereas a rapid thermodeactivation of these enzymes occurs at higher temperatures. In contrast to Xyl 1, the novel xylanase Xyl7A shows a prolonged thermostability at temperatures well above 70° C. when polymeric substrates such as wheat straw are used as substrates. The apparent temperature optimum for wheat straw hydrolysis is ~75° C. (FIG. 3). Therefore Xyl7A is active at higher temperatures compared to typical xylanases when hydrolysing complex biomass feedstocks such as wheat straw.

Example 6

Xylanase pH Optimum

Figure 4:
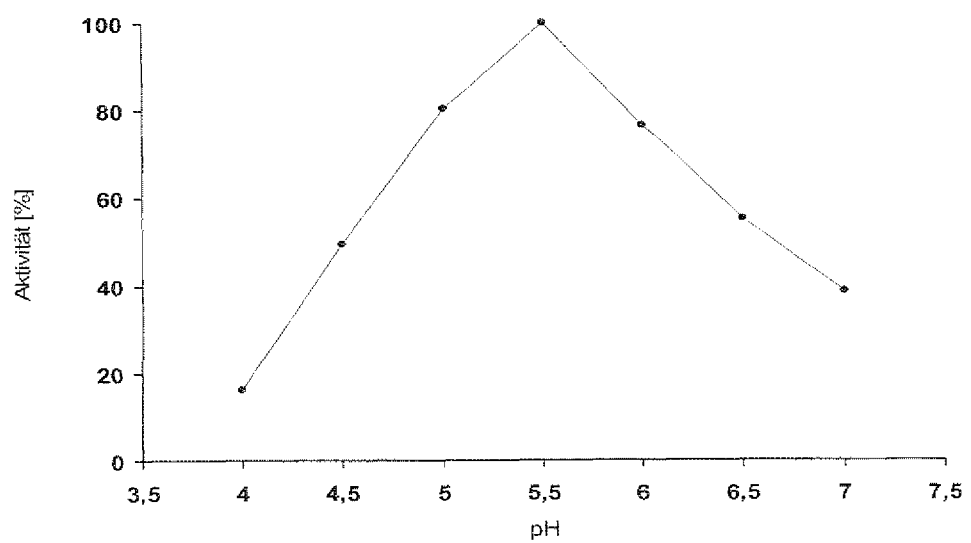
FIG. 4: Xyl7A pH activity profile

The operational pH range of Xyl7A was determined with pNP-Xylopyranoside as substrate under various pH buffer conditions (FIG. 4). The pH optimum is between pH 5 and 6.

The pH with the highest initial velocity (2.3 µM pNP/min) was designated as the 100% value shown. The specific activity at the optimal pH and optimal temperature is 86 µM/mg protein/min.

Example 7

Xylanase Thermostability in Buffer

To determine the apparent thermostability of Xyl7A in buffer, the enzyme was subjected to a primary incubation (30 min.) at different temperatures (50-80° C.) in a 50 mM NaAc buffer (pH 5). Subsequently, the samples where rapidly cooled and the remaining enzyme activity was determined relative to a standard using pNP xylopyranoside as substrate. The specific Xyl7A activity at 45° C. measured after 1 h with the pNP xylopyranoside was designated as 100% activity.

Figure 5:
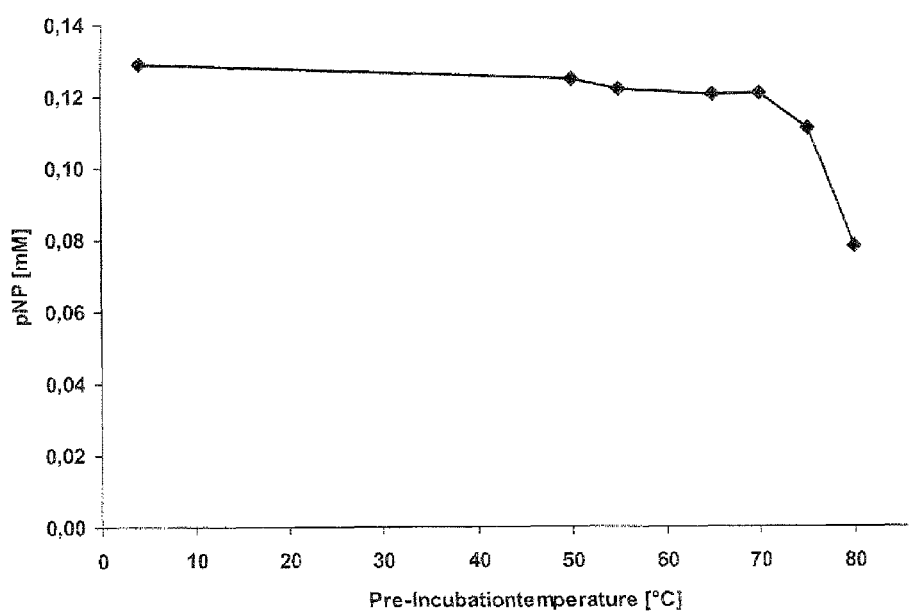
FIG. 5: Determination of apparent Xyl7A thermostability when pre-incubated for 30 min in 50 mM phosphate buffer at temperatures between 4 and 80° C.

The data in FIG. 5 show that under the reaction conditions Xyl7A retains more than 90% of its activity at temperatures up to 70° C. This data is consistent with results obtained for the hydrolysis of wheat straw over a 72 h period. The results indicate that Xyl 7A shows thermostability up to 70° C. without significant loss of activity even at long incubation times. This pronounced thermostability of Xyl7A is unusual for most endo-xylanases of fungal and bacterial origin, which commonly operate at moderate temperatures between 40-60° C. (Kulkani, N., Shendye, A., Rao, M. (1999) Molecular and biotechnological aspects of xylanases FEMS Microbiology Reviews 23, pp. 411-456). The marked temperature stability of Xyl7A allows for higher process temperatures and faster conversion rates for the depolymerisation of xylan.

Figure 7:
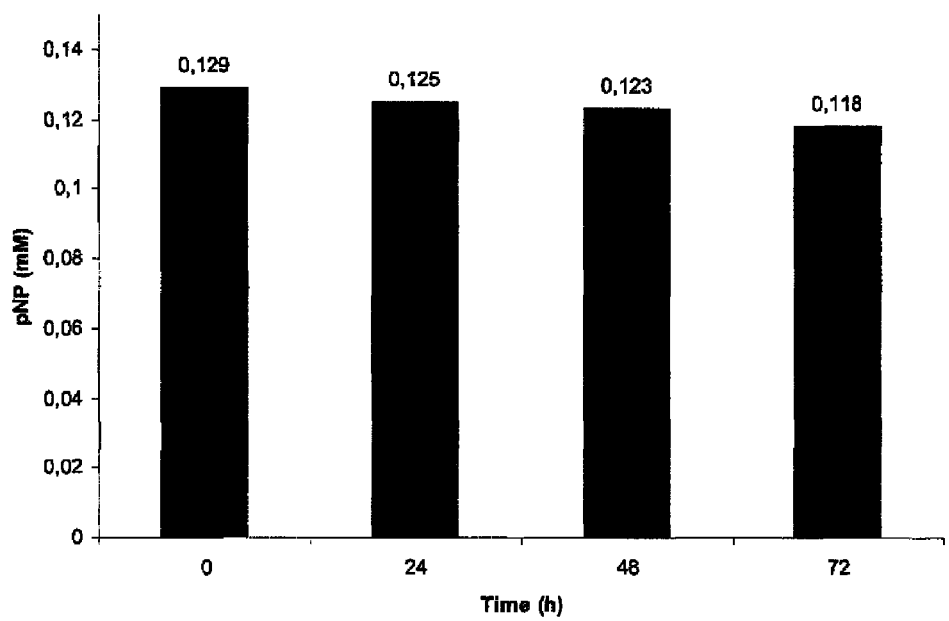
FIG. 7: Determination of Xyl7A thermostability as residual activity after 0 to 72 h incubation in 50 mM phosphate buffer at 70° C.

The long-term stability of Xyl7A was also determined. The Xylanase (0.05 g/l) was incubated in a 50 mM phosphate buffer at pH 5 for 0, 24, 48, 72 h at 70° C. The residual xylanase activity was subsequently measured at 45° C. with pNP Xylopyranoside (1 mM). The reaction was monitored for 1 h and the pNP-release was determined spectrophotometrically at 405 nm (FIG. 7). The residual activity after 72 h incubation at 70° C. is approximately 91% of its initial value.

Example 8

Protease Stability

Figure 6:
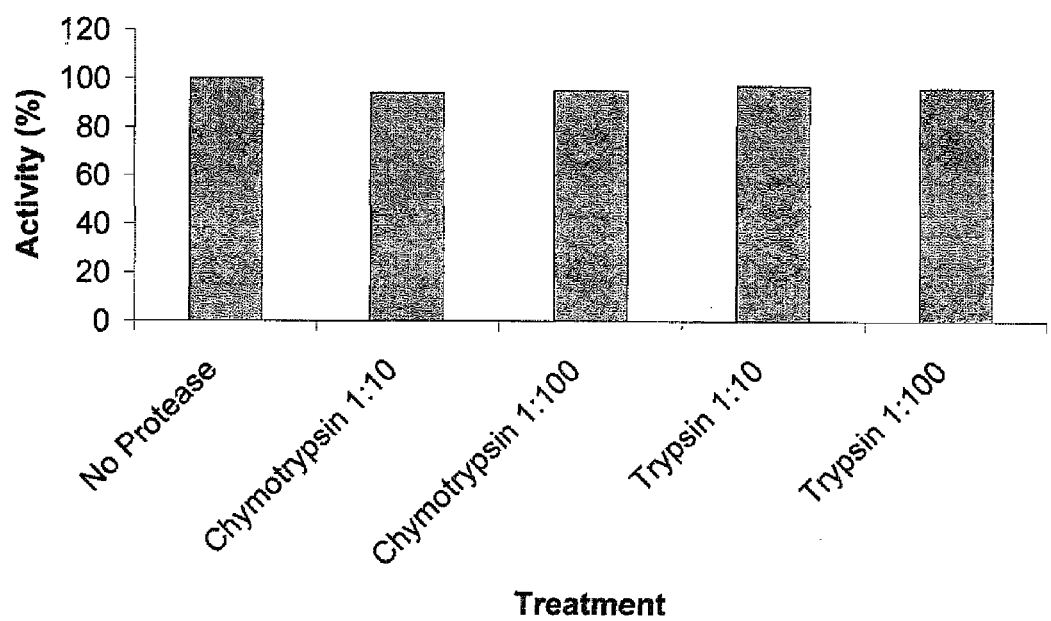
FIG. 6: Residual Xyl7A activity after 60 min protease treatment

Xyl7A was incubated with trypsin (Promega, Madison, Wis., USA, Cat. No.: V5280) and alternatively with chymotrypsin (Sigma, Weilheim, Germany, Cat. No.: CTRC) at a mass ratio of 1:10 and 1:100, respectively. The protease incubation was carried out in 50 mM NaAc buffer over time intervals of 0-60 min at the exact pH and temperature optimum for each protease (t=50° C., pH 7.8) according to the manufacturer protocols. The protease activity was stopped by adjusting the pH to 5.0 and measuring the residual Xyl7A activity using pNP-xylopyranoside as substrate (TAGUCHI, H., HAMASAKI, T., AKAMATSU, T., OKADA, H. (1996) A simple assay for xylanase using o-nitrophenyl-β-D-xylobioside. Bioscie. Biotechnol. Biochem. 60 (6), pp. 983-985). Xyl7A only showed marginal losses of enzyme activity even after an incubation period of 60 min with both, trypsin and chymotrypsin (FIG. 6). This significant alkaline protease resistance shown by Xyl7A is similar to the GH10 endo-xylanase from *Streptomyces fradiae* var. k11 (Li N, Yang P, Wang Y, Luo H, Meng K, Wu N, Fan Y, Yao B. (2008) Cloning, expression, and characterization of protease-resistant xylanase from *Streptomyces fradiae* var. k11. J Microbial Biotechnol. 18(3):410-416). However, in contrast to the *Streptomyces* enzyme which has a Topt of 60° C., Xyl7A as a significantly higher thermostability. The protease resistance of Xyl7A has a significant process advantage in food and feed applications as it prevents the deactivation of the enzyme by rumen microorganisms and gastrointestinal proteases during the feeding process.

```
                        Sequence Listings (protein sequence; mature protein, DNA = SEQ ID NO: 5)
                                                        SEQ ID NO: 1
LSNEEQYQLVVVREFNSVTPENVMKWDTIEPIRGQLNFEPADQLVDFARRHGQIVREHTLVWHNQLPS
WLTNGNFTNQELEEILRQHIYDVVRHFKGKVYSWDVVNEPLNEDGTLRDSIWLRAIGPDYIAKAFQWA
HEADPHAKLYINDYNIEWIGPKSNGMYELVKSLKEAGVPIDGVGFQGHLGIQYGFPGDIQQNIQREAD
LGLDVALSEVDVRMILPVTQEKLATQAEYYRRLMDACLNVRRCVSFTVWGFTDAHSWVPGFFQGQGAA
TIFDENYQPKPAYFALKDELTERSGRPQGKHYRNE (protein sequence; underlined: signal peptide, DNA = SEQ ID NO: 6)
                                                        SEQ ID NO: 2
LLGLRDYAARTHLSIGTAVDVNALSNEEQYQLVVVREFNSVTPENVMKWDTIEPIRGQLNFEPADQLV
DFARRHGQIVREHTLVWHNQLPSWLTNGNFTNQELEEILRQHIYDVVRHFKGKVYSWDVVNEPLNEDG
TLRDSIWLRAIGPDYIAKAFQWAHEADPHAKLYINDYNIEWIGPKSNGMYELVKSLKEAGVPIDGVGF
QGHLGIQYGFPGDIQQNIQRFADLGLDVALSEVDVRMILPVTQEKLATQAEYYRRLMDACLNVRRCVS
FTVWGFTDAHSWVPGFFQGQGAATIFDENYQPKPAYFALKDELTERSGRPQGKHYRNE (protein sequence; mature protein, DNA = SEQ ID NO: 7)
                                                        SEQ ID NO: 3
KRLGLRDYAARTHLSIGTAVDVNALSNEEQYQLVVVREFNSVTPENVMKWDTIEPIRGQLNFEPADQL
VDFARRHGQIVREHTLVWHNQLPSWLTNGNFTNQELEEILRQHIYDVVRHFKGKVYSWDVVNEPLNED
GTLRDSIWLRAIGPDYIAKAFQWAHEADPHAKLYINDYNIEWIGPKSNGMYELVKSLKEAGVPIDGVG
FQGHLGIQYGFPGDIQQNIQRFADLGLDVALSEVDVRMILPVTQEKLATQAEYYRRLMDACLNVRRCV
SFTVWGFTDAHSWVPGFFQGQGAATIFDENYQPKPAYFALKDELTERSGRPQGKHYRNE (protein sequence; underlined: MFa signal peptide, DNA = SEQ ID NO: 8)
                                                        SEQ ID NO: 4
MRFPSIFTAVLFAASSALAAPVNTTTEDETAQIPAEAVIGYSDLEGDFDVAVLPFSNSTNNGLLFINT
TIASIAAKEEGVSLDKRLGLRDYAARTHLSIGTAVDVNALSNEEQYQLVVVREFNSVTPENVMKWDTI
EPIRGQLNFEPADQLVDFARRHGQIVREHTLVWHNQLPSWLTNGNFTNQELEEILRQHIYDVVRHFKG
KVYSWDVVNEPLNEDGTLRDSIWLRAIGPDYIAKAFQWAHEADPHAKLYINDYNIEWIGPKSNGMYEL
VKSLKEAGVPIDGVGFQGHLGIQYGFPGDIQQNIQRFADLGLDVALSEVDVRMILPVTQEKLATQAEY
YRRLMDACLNVRRCVSFTVWGFTDAHSWVPGFFQGQGAATIFDENYQPKPAYFALKDELTERSGRPQG
KHYRNE (DNA sequence; mature protein only)
                                                        SEQ ID NO: 5
CTTTCTAATGAAGAACAATATCAGCTGGTGGTGGTCAGAGAATTCAATAGTGTTACCCCAGAAAATGT
CATGAAATGGGATACTATTGAGCCCATACGTGGTCAGCTAAATTTTGAGCCAGCAGATCAGCTCGTAG
ATTTTGCACGGCGGCATGGTCAGATAGTGAGAGAGCACACACTCGTCTGGCATAACCAACTGCCCAGC
TGGTTGACAAATGGTAACTTTACCAACCAGGAGCTGGAGGAAATACTGCGACAGCACATCTATGATGT
TGTAAGGCATTTCAAGGGCAAGGTGTATTCTTGGGACGTAGTGAACGAGCCCCTGAATGAAGATGGTA
CCCTAAGGGATAGCATATGGCTTAGGGCTATTGGTCCGGATTACATAGCCAAAGCTTTCCAATGGGCG
CACGAGGCTGATCCACATGCCAAACTCTACATCAATGACTACAACATTGAGTGGATCGGGCCTAAGAG
CAATGGAATGTACGAGCTGGTGAAGAGTCTCAAGGAAGCAGGTGTGCCTATCGATGGCGTGGGATTTC
AAGGACATCTCGGCATACAGTATGGATTTCCTGGGGATATTCAACAGAATATTCAGAGATTTGCTGAT
CTGGGATTGGATGTGGCTCTGTCTGAGGTGGATGTGCGCATGATTCTACCTGTTACCCAAGAGAAACT
TGCTACACAGGCTGAGTATTACCGTCGACTTATGGATGCTTGTCTGAATGTACGACGATGCGTATCTT
TCACAGTGTGGGGATTCACCGATGCTCACTCATGGGTACCCGGATTCTTCCAAGGACAAGGTGCGGCC
ACTATATTTGATGAGAATTATCAGCCGAAACCAGCGTATTTTGCTTTGAAGGATGAACTTACTGAGCG
TTCAGGTCGACCTCAGGGCAAACATTATAGGAACGAATAA (DNA sequence; underlined: signal peptide)
                                                        SEQ ID NO: 6
CTATTGGGTCTTCGAGACTATGCAGCAAGAACTCATCTTAGTATTGGAACAGCGGTA
GATGTAAATGCTCTTTCTAATGAAGAACAATATCAGCTGCTGGTGGTCAGAGAATTCAAT
AGTGTTACCCCAGAAAATGTCATGAAATGGGATACTATTGAGCCCATACGTGGTCAGCTA
AATTTTGAGCCAGCAGATCAGCTCGTAGATTTTGCACGGCGGCATGGTCAGATAGTGAGA
GAGCACACACTCGTCTGGCATAACCAACTGCCCAGCTGGTTGACAAATGGTAACTTTACC
AACCAGGAGCTGGAGGAAATACTGCGACAGCACATCTATGATGTTGTAAGGCATTTCAAG
GGCAAGGTGTATTCTTGGGACGTAGTGAACGAGCCCCTGAATGAAGATGGTACCCTAAGG
GATAGCATATGGCTTAGGGCTATTGGTCCGGATTACATAGCCAAAGCTTTCCAATGGGCG
CACGAGGCTGATCCACATGCCAAACTCTACATCAATGACTACAACATTGAGTGGATCGGG
CCTAAGAGCAATGGAATGTACGAGCTGGTGAAGAGTCTCAAGGAAGCAGGTGTGCCTATC
GATGGCGTGGGATTTCAAGGACATCTCGGCATACAGTATGGATTTCCTGGGGATATTCAA
CAGAATATTCAGAGATTTGCTGATCTGGGATTGGATGTGGCTCTGTCTGAGGTGGATGTG
CGCATGATTCTACCTGTTACCCAAGAGAAACTTGCTAGACAGGCTGAGTATTACCGTCGA
```

```
CTTATGGATGCTTGTCTGAATGTACGACGATGCGTATCTTTCACAGTGTGGGGATTCACC
GATGCTCACTCATGGGTACCCGGATTCTTCCAAGGACAAGGTGCGGCCACTATATTTGAT
GAGAATTATCAGCCGAAACCAGCGTATTTTGCTTTGAAGGATGAACTTACTGAGCGTTCA
GGTCGACCTCAGGGCAAACATTATAGGAACGAATAA
```

(DNA sequence; mature mod. protein only)

SEQ ID NO: 7

```
AAGAGATTGGGACTGAGAGATTACGCTGCTAGAACCCACTTGTCTATCGGAACCGCCGTTGACGTTAA
CGCTCTGTCTAACGAGGAACAGTACCAGCTGGTTGTTGTGAGAGAGTTCAACTCTGTTACCCCAGAGA
ACGTGATGAAGTGGGACACCATCGAGCCAATTAGAGGACAGCTGAACTTTGAGCCAGCTGACCAGTTG
GTTGACTTCGCTAGAAGACACGGACAGATTGTGAGAGAGCACACCCTTGTTTGGCACAACCAGCTGCC
ATCTTGGTTGACCAACGGCAACTTCACCAACCAGGAACTGGAAGAGATTCTGAGACAGCACATCTACG
ACGTTGTGAGACACTTGAAGGGCAAGGTGTACTCTTGGGACGTTGTTAACGAGCCATTGAACGAGGAC
GGTACTCTGAGAGACTCTATCGGCTGAGAGCTATCGGTCCAGACTACATCGCTAAGGCTTTTCAGTG
GGCTCACGAAGCTGATCCACACGCCAAGCTGTACATCAACGACTACAACATCGAGTGGATCGGTCCAA
AGTCTAACGGAATGTACGAGCTGGTGAAGTCTTTGAAAGAGGCCGGCGTTCCTATTGATGGTGTTGGT
TTCCAGGGTCACCTGGGTATTCAGTACGGTTTCCCAGGTGACATCCAGCAGAACATCCAGAGATTTGC
TGACCTGGGACTGGATGTTGCTTTGTCTGAAGTGGATGTGAGAATGATCCTGCCAGTGACCCAGGAAA
AGTTGGCTACTCAGGCCGAGTACTATAGAAGATTGATGGACGCCTGCCTGAATGTTAGAAGATGCGTG
TCTTTCACTGTGTGGGTTTTACTGACGCTCACTCTTGGGTTCCAGGATTCTTTCAGGGTCAAGGTGC
CGCTACTATCTTCGACGAGAACTACCAGCCAAAGCCAGCTTACTTTGCCTTGAAGGACGAGTTGACCG
AGAGATCTGGTAGACCACAGGGAAAGCACTACAGAAACGAGTAA
```

(DNA sequence; underlined: signal peptide)

SEQ ID NO: 8

```
atgagatttccttcaattttttactgcagttttattcgcagcatcctccgcattagctgctccagtcaa
cactacaacagaagatgaaacggcacaaattccggctgaagctgcatcggttactcagatttagaag
gggatttcgatgttgctgttttgccattttccaacagcacaaataacgggttattgtttataaatact
actattgccagcattgctgctaaagaagaaggggtaagcttggatAAGAGATTGGGACTGAGAGATTA
CGCTGCTAGAACCCACTTGTCTATCGGAACCGCCGTTGACGTTAACGCTCTGTCTAACGAGGAACAGT
ACCAGCTGGTTGTTGTGAGAGAGTTCAACTCTGTTACCCCAGAGAACGTGATGAAGTGGGACACCATC
GAGCCAATTAGAGGACAGCTGAACTTTGAGCCAGCTGACCAGTTGGTTGACTTCGCTAGAAGACACGG
ACAGATTGTGAGAGAGCACACCCTTGTTTGGCACAACCAGCTGCCATCTTGGTTGACCAACGGCAACT
TCACCAACCAGGAACTGGAAGAGATTCTGAGACAGCACATCTACGACGTTGTGAGACACTTCAAGGGC
AAGGTGTACTCTTGGGACGTTGTTAACGAGCCATTGAACGAGGACGGTACTCTGAGAGACTCTATCTG
GCTGAGAGCTATCGGTCCAGACTACATCGCTAAGGCTTTTCAGTGGGCTCACGAAGCTGATCCACACG
CCAAGCTGTACATCAACGACTACAACATCGAGTGGATCGGTCCAAAGTCTAACGGAATGTACGAGCTG
GTGAAGTCTTTGAAAGAGGCCGGCGTTCCTATTGATGGTGTTGGTTTCCAGGGTCACCTGGGTATTCA
GTACGGTTTCCCAGGTGACATCCAGCAGAACATCCAGAGATTTGCTGACCTGGGACTGGATGTTGCTT
TGTCTGAAGTGGATGTGAGAATGATCCTGCCAGTGACCCAGGAAAAGTTGGCTACTCAGGCCGAGTAC
TATAGAAGATTGATGGACGCCTGCCTGAATGTTAGAAGATGCGTGTCTTTCACTGTGTGGGTTTTAC
TGACGCTCACTCTTGGGTTCCAGGATTCTTTCAGGGTCAAGGTGCCGCTACTATCTTCGACGAGAACT
ACCAGCCAAAGCCAGCTTACTTTGCCTTGAAGGACGAGTTGACCGAGAGATCTGGTAGACCACAGGGA
AAGCACTACAGAAACGAGtaa
```

The invention claimed is:

1. An isolated polypeptide having xylanase activity which maintains at least 80% of its xylanase activity after 72 hours incubation in 50 mM phosphate buffer at 70° C., wherein the polypeptide has the sequence as defined by SEQ ID No: 1 or SEQ ID No: 2 or SEQ ID No: 3 or SEQ ID No: 4, or a sequence as defined by SEQ ID No: 1 or SEQ ID No: 2 or SEQ ID No: 3 or SEQ ID No: 4, wherein any 1 to 30 amino acid residues are substituted, deleted, or inserted.

2. The polypeptide according to claim 1, wherein the polypeptide yields xylose and glucose in a weight ratio of at least 10:1 when subjecting wheat straw to the polypeptide at pH 5 and 45° C.

3. The polypeptide according to claim 1, wherein the polypeptide shows optimum xylanase activity in the pH range of 5-6.

4. The polypeptide according to claim 1, wherein the polypeptide comprises an amino acid sequence having at least 95%, sequence identity to the SEQ ID No: 1.

5. The polypeptide according to claim 1, wherein the polypeptide maintains at least 80% of its xylanase activity after having been subjected to trypsin at pH 7.8 and 50° C. for 1 hour.

6. The polypeptide according toslaim 1, wherein the xylanase shows an optimum activity for the hydrolysis of xylose from wheat straw in the temperature range between 45 and 80° C.

7. The polypeptide according to claim 1, which is expressed and secreted at a level of more than 100 mg/l, more preferably of more than 1 g/l into the supernatant after introduction of a nucleic acid encoding a polypeptide having an amino acid sequence with at least 95% sequence identity to the SEQ ID No: 1 into a yeast.

8. Composition comprising the polypeptide of claim 1 and a cellulase.

9. The polypeptide according to claim 1, wherein the polypeptide comprises an amino acid sequence having at least 95% sequence identity to the SEQ ID No: 1.

10. The polypeptide according to claim 1, wherein the polypeptide maintains at least 90% of its xylanase activity after having been subjected to trypsin at pH 7.8 and 50° C. for 1 hour.

11. The polypeptide according to claim 1, wherein the xylanase shows an optimum activity for the hydrolysis of xylose from wheat straw in the temperature range between 65 and 75° C.

12. A method for enzymatic degradation of lignocellulosic biomass, the method comprising contacting a lignocellulosic biomass with a polypeptide according to claim 1, such that the lignocellulosic biomass is degraded.

\* \* \* \* \*